US012766111B2

(12) United States Patent
Dahlman et al.

(10) Patent No.: US 12,766,111 B2
(45) Date of Patent: Oct. 20, 2026

(54) IONIZABLE LIPIDS WITH BIOACTIVE MOTIFS

(71) Applicant: GEORGIA TECH RESEARCH CORPORATION, Atlanta, GA (US)

(72) Inventors: James Dahlman, Atlanta, GA (US); Marine Z.C. Hatit, Atlanta, GA (US); Huanzhen Ni, Carmel, IN (US)

(73) Assignee: Georgia Tech Research Corporation, Atlanta, GA (US)

( * ) Notice: Subject to any disclaimer, the term of this patent is extended or adjusted under 35 U.S.C. 154(b) by 298 days.

(21) Appl. No.: 18/723,199

(22) PCT Filed: Dec. 20, 2022

(86) PCT No.: PCT/US2022/082048
§ 371 (c)(1),
(2) Date: Jun. 21, 2024

(87) PCT Pub. No.: WO2023/122611
PCT Pub. Date: Jun. 29, 2023

(65) Prior Publication Data

US 2025/0127727 A1 Apr. 24, 2025

Related U.S. Application Data

(60) Provisional application No. 63/293,287, filed on Dec. 23, 2021.

(51) Int. Cl.

| | |
|---|---|
| ***A61K 9/51*** | (2006.01) |
| ***A61K 31/7105*** | (2006.01) |
| ***C07D 295/13*** | (2006.01) |

(52) U.S. Cl.
CPC .......... *A61K 9/5123* (2013.01); *A61K 9/5146* (2013.01); *A61K 31/7105* (2013.01); *C07D 295/13* (2013.01)

(58) Field of Classification Search
CPC ................ A61K 9/5123; A61K 9/5146; A61K 31/7105; A61K 9/1271; A61K 9/0019; C07D 295/13
See application file for complete search history.

(56) References Cited

U.S. PATENT DOCUMENTS 9,290,779 B1 3/2016 Juckem et al.

FOREIGN PATENT DOCUMENTS

WO 2021021634 A1 2/2021

OTHER PUBLICATIONS

Pubchem, SID 108431397, Modify Date: May 31, 2019 [retrieved on 21 Feb. 1-3, 2023]., Retrieved from the Internet <URL: https://pubchem.ncbi.nim.nih.gov/substance/108431397> entire document.
Ni et al., Piperazine-derived lipid nanoparticles deliver mRNA to immune cells in vivo, Nature 1-3 Communications, vol. 13, Article 4766, Aug. 15, 2022 [retrieved on Apr. 20, 2023]. Retrieved from the Internet: <URL: https:/Avww.nature.com/articles/s41467-022-32281-5>. pp. 1-9.
Pubchem, SID 475724931, Available Date: Feb. 4, 2023 [retrieved on Apr. 15, 2023]., Retrieved from the Internet <URL: https://pubchem.ncbi.nim.nih.gov/substance/475724931> entire document.

*Primary Examiner* — Robert A Wax
*Assistant Examiner* — Kimberly Barber
(74) *Attorney, Agent, or Firm* — BakerHostetler

(57) ABSTRACT

Provided are ionizable lipids containing a piperazine moiety, as well as lipid nanoparticles that can be formed using the ionizable lipids for use in delivering nucleic acids and other therapeutic agents to specific cell types.

27 Claims, 6 Drawing Sheets

IONIZABLE LIPIDS WITH BIOACTIVE MOTIFS

CROSS-REFERENCE TO RELATED APPLICATIONS

This application is a U.S. national stage of International Patent Application No. PCT/US2022/082048, filed on Dec. 20, 2022, which claims the benefit of priority to U.S. Provisional Application No. 63/293,287, filed Dec. 23, 2021, the entire contents of both of which are incorporated herein by reference.

GOVERNMENT RIGHTS

This invention was made with government support under Contract No. UG3-TR002855 awarded by the National Institutes of Health, and Contract No. HR00111920008 awarded by the Defense Advanced Research Projects Agency. The government has certain rights in the invention.

TECHNICAL FIELD

The present disclosure concerns ionizable lipids that can be used to form lipid nanoparticles (LNPs).

BACKGROUND

In humans, lipid nanoparticles (LNPs) have safely delivered therapeutic RNA to hepatocytes after systemic administration and to antigen-presenting cells after intramuscular injection. The Food and Drug Administration (FDA) approved its first lipid nanoparticle (LNP)-based siRNA drug to treat an inherited genetic disease in 2018[1]. Since then, systemically administered siRNA therapeutics have been approved to treat three additional liver diseases[2-4] and generated promising earlier-stage mRNA[5] clinical data. Similarly, intramuscularly administered mRNA therapies have been FDA approved[6] or been given Emergency Use Authorization[7] to vaccinate against coronavirus disease of 2019. Unfortunately, there have also been clinical failures driven by insufficient delivery[8-9]. Taken together, the efficacy of approved RNA vaccines and liver therapies underscores the potential clinical impact of LNPs with tropism to new cell types. However, this challenge is stark; no systemically administered LNP carrying an RNA drug has yet reached phase III clinical trials, let alone been FDA approved.

Delivering RNA to non-hepatocytes has remained challenging in large part due to the anatomy and physiology of the liver. Specifically, the hepatic sinusoids contain a discontinuous vasculature[10] as well as slow blood flow[11]; both increase nanoparticle extravasation and subsequent interactions with hepatocytes. To target non-hepatocytes, scientists have used two approaches. In the first approach, an LNP with tropism to hepatocytes is retargeted with an active targeting ligand. For example, LNPs made with DLin-MC3-DMA[12], an ionizable lipid that is FDA approved for hepatocyte siRNA delivery[13], have been retargeted to immune cells using a lipid-bound antibody[14-17]. One potential limitation of this approach is that actively targeted nanoparticles containing RNA drugs have led to adverse events in clinical trials[18]. In a second approach, scientists identify nanoparticles that interact with natural trafficking pathways, thereby leading to endogenous targeting[19]. Although these approaches have led to an FDA approval[13] and promising phase 1 clinical data[5], this second approach also has a key limitation. After synthesizing a large, chemically diverse lipid library, scientists must evaluate how each nanoparticle delivers its payload into cells. Since injecting and sacrificing thousands of mice per library is unethical, this screening is performed in vitro (i.e., in cell culture). For example, across three representative papers[20-22], labs tested 4,736 nanoparticles in vitro, using the data to select 14 nanoparticles for in vivo studies. However, this screening method is likely inefficient, given that in vitro nanoparticle delivery can be a poor predictor of in vivo nanoparticle delivery[23].

Systemic RNA delivery to non-hepatocytes remains challenging, especially without targeting ligands such as antibodies, peptides, or aptamers.

SUMMARY

Provided herein are compounds of Formula (I) representing ionizable lipids:

(I)

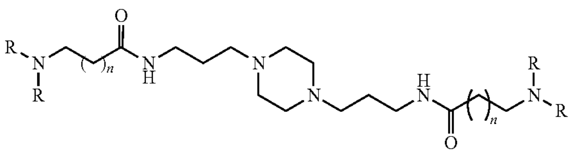

wherein each R is $C_{10-18}$ alkyl or alkenyl; and, n is 1 or 2.

Also disclosed are lipid nanoparticles comprising a compound of Formula (I), as well as methods comprising administering to a subject the presently disclosed lipid nanoparticles, wherein a therapeutic agent may be encapsulated within the lipid nanoparticles.

DETAILED DESCRIPTION OF ILLUSTRATIVE EMBODIMENTS

Figure 1:
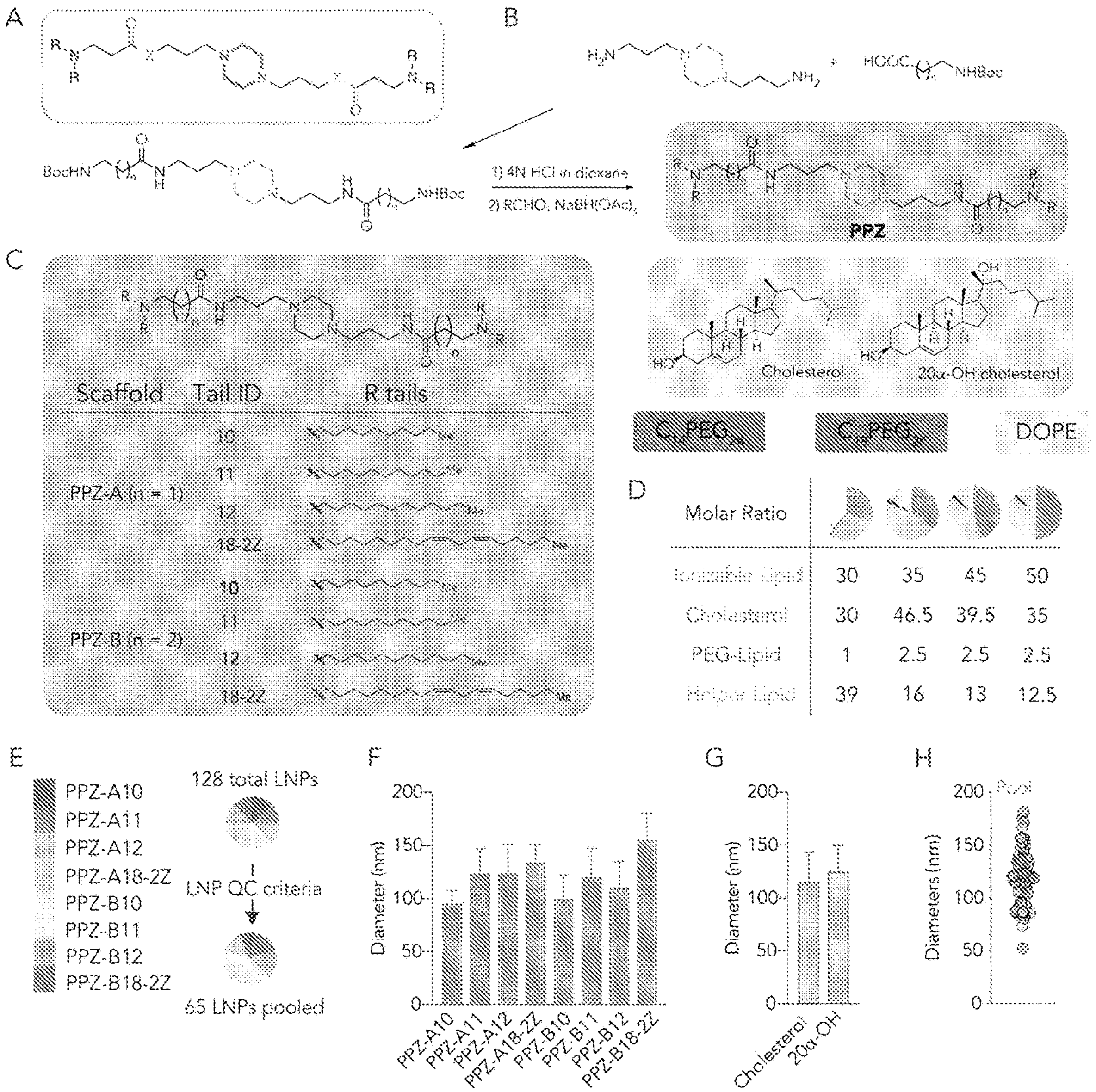
FIGS. 1A-1H illustrate the processes and parameters with which piperazine-based lipids were used to formulate stable lipid nanoparticles (LNPs).

The present invention may be understood more readily by reference to the following detailed description taken in connection with the accompanying examples, which form a part of this disclosure. It is to be understood that this invention is not limited to the specific products, methods, conditions or parameters described and/or shown herein, and that the terminology used herein is for the purpose of describing particular embodiments by way of example only and is not intended to be limiting of the claimed invention.

The disclosures of each patent, patent application, and publication cited or described in this document are hereby incorporated herein by reference, in their entirety.

As employed above and throughout the disclosure, the following terms and abbreviations, unless otherwise indicated, shall be understood to have the following meanings.

In the present disclosure the singular forms "a", "an", and "the" include the plural reference, and reference to a particular numerical value includes at least that particular value, unless the context clearly indicates otherwise. Thus, for example, a reference to "a compound" is a reference to one or more of such compounds and equivalents thereof known to those skilled in the art, and so forth. Furthermore, when indicating that a certain chemical moiety "may be" X, Y, or Z, it is not necessarily intended by such usage to exclude other choices for the moiety; for example, a statement to the effect that $R_1$ "may be alkyl, aryl, or amino" does not necessarily exclude other choices for $R_1$, such as halo, aralkyl, and the like.

When values are expressed as approximations, by use of the antecedent "about," it will be understood that the particular value forms another embodiment. As used herein, "about X" (where X is a numerical value) preferably refers to ±10% of the recited value, inclusive. For example, the phrase "about 8" may refer to a value of 7.2 to 8.8, inclusive; as another example, the phrase "about 8%" may refer to a value of 7.2% to 8.8%, inclusive. Where present, all ranges are inclusive and combinable. For example, when a range of "1 to 5" is recited, the recited range should be construed as including ranges "1 to 4", "1 to 3", "1-2", "1-2 & 4-5", "1-3 & 5", and the like. In addition, when a list of alternatives is positively provided, such listing can be interpreted to mean that any of the alternatives may be excluded, e.g., by a negative limitation in the claims. For example, when a range of "1 to 5" is recited, the recited range may be construed as including situations whereby any of 1, 2, 3, 4, or 5 are negatively excluded; thus, a recitation of "1 to 5" may be construed as "1 and 3-5, but not 2", or simply "wherein 2 is not included." In another example, when a listing of possible substituents including "hydrogen, alkyl, and aryl" is provided, the recited listing may be construed as including situations whereby any of "hydrogen, alkyl, and aryl" is negatively excluded; thus, a recitation of "hydrogen, alkyl, and aryl" may be construed as "hydrogen and aryl, but not alkyl", or simply "wherein the substituent is not alkyl".

Protective groups are abbreviated according to the system disclosed in Greene, T. W. and Wuts, P. G. M., *Protective Groups in Organic Synthesis 2d. Ed.*, Wiley & Sons, 1991, which is incorporated in its entirety herein. For example, "CBZ" or "Cbz" or "Z" stands for carbobenzyloxy or benzyloxycarbonyl, "Boc" or "BOC" represents t-butoxycarbonyl, "Alloc" denotes allyloxycarbonyl, Bz means benzoyl, and "Fmoc" stands for 9-fluorenylmethoxycarbonyl.

As used herein, the terms "component", "compound", "drug", "pharmacologically active agent", "active agent", "therapeutic", "therapeutic agent", "therapy", "treatment", or "medicament" may be used herein to refer to a compound or compounds or composition of matter which, when administered to a subject (human or animal) induces a desired pharmacological and/or physiologic effect by local and/or systemic action.

As used herein, "alkyl" refers to an optionally substituted, saturated straight, or branched, hydrocarbon radical having from about 1 to about 20 carbon atoms (and all combinations and subcombinations of ranges and specific numbers of carbon atoms therein). Where appropriate, "alkyl" can mean "alkylene"; for example, if X is $—R_1R_2$, and $R_1$ is said to be "alkyl", then "alkyl" may correctly be interpreted to mean "alkylene".

As used herein, "alkenyl" refers to an alkyl radical having from about 2 to about 20 carbon atoms and one or more double bonds (and all combinations and subcombinations of ranges and specific numbers of carbon atoms therein), wherein alkyl is as previously defined. In some embodiments, it is preferred that the alkenyl groups have from about 2 to about 6 carbon atoms. Alkenyl groups may be optionally substituted.

Disclosed herein are piperazine-containing ionizable lipids (Pi-Lipids) that can, among other things, preferentially deliver mRNA to immune cells in vivo without targeting ligands. The inventive Pi-Lipids were synthesized and characterized, and high-throughput DNA barcoding was used to quantify how 65 chemically distinct LNPs functionally delivered mRNA (i.e., mRNA translated into functional, gene-editing protein) in 14 cell types directly in vivo. By analyzing the relationships between lipid structure and cellular targeting, lipid traits that increase delivery in vivo were identified. In addition, LNPs that preferentially delivers mRNA to liver and splenic immune cells at the clinically relevant dose of 0.3 mg/kg were prepared and characterized. The obtained data highlighted inventive nanoparticles with natural non-hepatocyte tropism and demonstrated that the presently disclosed lipids with bioactive small-molecule motifs successfully deliver mRNA in vivo.

Accordingly, disclosed are compounds of Formula (I) representing ionizable lipids:

(I)

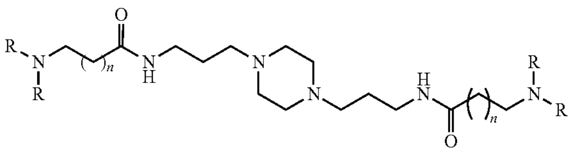

wherein each R is $C_{10-18}$ alkyl or alkenyl; and, n is 1 or 2.

Each R within the compound of Formula (I) may be the same. In some embodiments, the respective R groups may be the same as one, two, or three of the other R groups. In other instances, a particular R group may be different from one, two, or each of the other R groups.

As noted, each R is $C_{10-18}$ alkyl or alkenyl. For example, R may be $C_{10}$alkyl, $C_{11}$alkyl, $C_{12}$alkyl, $C_{13}$alkyl, $C_{14}$alkyl, $C_{15}$alkyl, $C_{16}$alkyl, $C_{17}$alkyl, or $C_{18}$alkyl. In some embodiments, each R is $C_{10}$ alkyl or $C_{11}$alkyl.

In other embodiments, R may be $C_{10}$alkenyl, $C_{11}$alkenyl, $C_{12}$alkenyl, $C_{13}$alkenyl, $C_{14}$alkenyl, $C_{15}$alkenyl, $C_{16}$alkenyl, $C_{17}$alkenyl, or $C_{18}$alkenyl. When R is $C_{10-18}$alkenyl, the placement of respective double bonds may be between any of the carbon atoms forming the carbon chain. For example, the double bond may be between any one or more of C1 and C2, C2 and C3, C3 and C4, C4 and C5, C5 and C6, C6 and C7, C7 and C8, C8 and C9, C9 and C10, C10 and C11, C11 and C12, C12 and C13, C13 and C14, C14 and C15, C15 and C16, C16 and C17, or C17 and C18. The number of double bonds within the carbon chain may be, for example, one, two, three, four, five, six, seven, eight, nine, or ten. In some embodiments, each R is octadeca-9,12-dienyl.

In certain embodiments, R is $C_{10}$alkyl and n is 1. In other instances, R is $C_{10}$alkyl and n is 2. In certain other embodiments, R is $C_{11}$alkyl and n is 1. In other instances, R is $C_{11}$alkyl and n is 2. In particular embodiments, R is $C_{18}$ alkenyl, and n is 1. In other instances, R is $C_{18}$ alkenyl, and n is 2. The present compounds may also be such that each R is octadeca-9,12-dienyl, and n is 1. In other embodiments, each R is octadeca-9,12-dienyl, and n is 2.

Also disclosed herein are lipid nanoparticles comprising a compound of Formula (I) according to any one of the embodiments described herein. The present lipid nanoparticles may further comprise one or more of a helper lipid, a cholesterol, and a polyethylene glycol (PEG) lipid. Advantageously, the lipid nanoparticles according to the present disclosure that include a compound of Formula (I) deliver a therapeutic agent, such as a nucleic acid, preferentially to liver or splenic cells of the subject. Such preferential delivery occurs without the requirement for a specific targeting ligand. For example, the presently disclosed lipid nanoparticles can deliver a therapeutic agent preferentially to liver Kupffer cells, spleen dendritic cells, spleen macrophages, liver endothelial cells, or liver dendritic cells. As used herein, preferential delivery to a particular class of cells or cell type refers to delivery at a higher rate than to non-targeted cells. For example, the preferential delivery can mean delivery at or above a rate that is at least 1, 2, 3, 4, 5, 6, 7, 8, 9, 10, 20, 50, or 100 times greater than to non-targeted cells, i.e., cells not within the particular class of cells or of the particular cell type. In some instances, the delivery is to a particular targeted class of cells or cell type, and there is no delivery or only minimal delivery to non-targeted cells. As a result, the preferential delivery can be at a rate that is hundreds of times, thousands of times, or, theoretically infinitely greater than to the non-targeted cells.

The role and identity of exemplary helper lipids for lipid nanoparticles are known among those skilled in the art may be any compound that contributes to the stability and delivery efficiency of the LNP, or to the stable encapsulation of a therapeutic agent within the LNP. Helper lipids with cone-shape geometry favoring the formation hexagonal II phase, such as dioleoylphosphatidylethanolamine (DOPE, also described as 1,2-dioeoyl-sn-glycero-3-phosphoethanolamine), can promote favorable LNP characteristics. Certain embodiments of the presently disclosed lipid nanoparticles comprise DOPE, in addition to the compound of Formula (I). In other embodiments, cylindrical-shaped lipid phosphatidylcholine can be included in order provide bilayer stability, which may assist with in vivo application of LNPs. Distearolyphosphatidycholine or DSPC represents an exemplary helper lipid. Further exemplary helper lipids include 1,2-dioleoyl-sn-glycero-3-phosphoethanolamine, 1,2-dioleoyl-3-trimethylammonium-propane (chloride salt), and dimethyldioctadecylammonium (bromide salt). Other helper-type lipids can be selected based on the particular requirements for the lipid nanoparticle, and any such helper lipid can be used in accordance with the present disclosure.

The presently disclosed lipid nanoparticles may also include a cholesterol, or a combination of two or more cholesterols. The inclusion of a cholesterol in nanoparticle formulations has been shown to improve efficacy, potentially due to enhanced membrane fusion. As used herein "a cholesterol" may refer to a cholesterol analog or derivative. Exemplary cholesterol species include cholesterol ($C_{27}H_{46}O$), 20α-OH cholesterol, and 20α-hydroxycholesterol (5-cholestene-3β,20α-diol). Any natural sterol may also be used for the cholesterol component. Examples of natural sterols include, for example, cholesterol sulfate, desmosterol, stigmasterol, lanosterol, 7-dehydrocholesterol, dihydrolanosterol, zymosterol, lathosterol, 14-demethyllanosterol, 8(9)-dehydrocholesterol, 8(14)-dehydrocholesterol, FF-MAS, diosgenin, DHEA sulfate, DHEA, sitosterol, lanosterol-95, cholesterol (plant), dihydro FF-MAS-d6, dihydro T-MAS-d6, zymostenol, sitostanol, campestanol, campesterol, 7-dehydrodesmosterol, pregnenolone, dihydro T-MAS, delta 5-avenasterol, brassicasterol, dihydro FF-MAS, and 24-methylene cholesterol. A large diversity of structural analogs of cholesterol exist as natural products (e.g., phytosterols that are plant-based sterols, which provide stability to the plant cell wall). Exemplary cholesterol analogs include, for example, Vitamin D derivatives (such as 9,10-secosteroids, Vitamin D2, Vitamin D3, Calcipotriol), alkyl-substituted steroids (such as C-24 alkyl steroids), and cholesterol analogs wherein the tail is modified into a fifth ring (such as pentacyclic steroids).

The lipid nanoparticles according to the present disclosure may also include a polyethylene glycol (PEG) lipid. The PEG lipid can function, for example, to coat the surface of nanoparticles ("PEGylation"), in order to improve the efficiency of delivery of a therapeutic agent to target cells and tissues. Numerous PEG lipids have been developed for use in lipid nanoparticles, and PEG lipids are otherwise a genus of lipids of which any may be selected for use in accordance with the present disclosure. For example, the PEG lipid may feature a branched or linear PEG chain conjugated with one or more lipid tails. Exemplary lipid tails include distearyl phosphatidylethanolamine (DSPE) or dimyristoyl glycerol (DMG). PEG lipids can include, for example, mPEG-DMG, DSPE-PEG-DSPE, mPEG-CLS, mPEG-DSPE, mPEG-DMPE, mPEG-DPPE, mPEG-DLPE, mPEG-DOPE, DSPE-PEG-OH, DSPE-PEG-SH, DSPE-PEG-CHO, or DSPE-PEG-$NH_2$. Other exemplary PEG lipids include $C_{8-20}PEG_x$, wherein x designates the molecular weight of the PEG and can be about 500-10,000, 500-7,500, 750-6,000, 800-6,000, 900-5,500, or 1,000-5,000 Dalton. For example, the PEG lipid may be $C_{14}PEG_{2K}$ or $C_{18}PEG_{2K}$.

In some embodiments of the presently disclosed LNPs, in addition to the compound of Formula (I), the helper lipid is dioleoylphosphatidylethanolamine, the cholesterol is cholesterol ($C_{27}H_{46}O$) or 20α-OH cholesterol, and the PEG lipid is $C_{14}PEG_{2K}$ or $C_{18}PEG_{2K}$. With respect to such embodiments, the compound of Formula (I) may be such that R is $C_{10}$ alkyl, $C_{11}$alkyl, or octadeca-9,12-dienyl.

The molar ratio of the compound according to Formula (I):the helper lipid:the cholesterol:the PEG lipid in the present lipid nanoparticles may be about 30-50:30-47:1-3:12-40. In certain embodiments, the molar ratio of the compound according to Formula (I):the helper lipid:the cholesterol:the PEG lipid is about 30-40:40-47:1-3:12-20. In particular embodiments, the molar ratio of the compound according to Formula (I):the helper lipid:the cholesterol:the PEG lipid is about 35:46.5:2.5:16.

Thus, the molar concentration of the compound according to Formula (I) in the present LNPs may be about 30, 31, 32, 33, 34, 35, 36, 37, 38, 39, 40, 41, 42, 43, 44, 45, 46, 47, 48, 49, or 50. The molar concentration of the helper lipid in the present LNPs may be about 30, 31, 32, 33, 34, 35, 36, 37, 38, 39, 40, 41, 42, 43, 44, 45, 46, or 47. The molar concentration of the cholesterol in the present LNPs may be about 1, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0. The molar concentration of the PEG lipid may be about 12, 13, 14, 15, 16, 17, 18, 19, 20, 21, 22, 23, 24, 25, 26, 27, 28, 29, 30, 31, 32, 33, 34, 35, 36, 37, 38, 39, or 40.

The lipid nanoparticle may have a diameter of about 20-400 nm. For example, the diameter of the lipid nanoparticle may be about 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, or 400 nm. In a given population of lipid nanoparticles according to the present disclosure, the population may include individual members of respectively different sizes. The particle size distribution of a given population of LNPs according to the present disclosure may be characterized by a D90 of about 400, 390, 380, 370, 360, 350, 340, 330, 320, 310, 300, 290, 280, 270, 260, 250, 240, 230, 220, 210, 200, 190, 180, 170, 160, 150, 140, 130, 120, 110, or 100 nm, and/or a D10 of about 10, 20, 30, 40, 50, 60, 70, 80, 90, 100, 110, 120, 130, 140, 150, 160, 170, 180, 190, or 200 nm.

The lipid nanoparticles according to the present disclosure can be used for the delivery of therapeutic agents to a living organism, such as to a human subject. The therapeutic agent may be encapsulated within the lipid nanoparticle. Lipid nanoparticles as a general class have been thoroughly investigated and successfully entered the clinic for the delivery of small molecules, siRNA drugs, and mRNA. In accordance with the present disclosure, the therapeutic agent that is encapsulated within the lipid nanoparticle may be a nucleic acid, oligonucleotide, polynucleotide, protein, peptide, carbohydrate, glycoprotein, lipid, small molecule, or any combination thereof. In some embodiments, the therapeutic agent is a small molecule, siRNA, or mRNA.

Also provided herein are methods comprising administering to a subject a lipid nanoparticle according to any of the presently disclosed embodiments, wherein the lipid nanoparticle comprises a therapeutic agent. It has surprisingly been discovered that the inventive nanoparticles preferentially target human liver and splenic cells, and can thereby preferentially deliver the therapeutic agent to such cells. The cells to which the present LNPs deliver the therapeutic agent can include, for example, liver Kupffer cells, spleen dendritic cells, spleen macrophages, liver endothelial cells, or liver dendritic cells. Accordingly, the present disclosure also provides methods for delivering a therapeutic agent to liver or splenic cells of a subject, comprising administering to the subject a lipid nanoparticle according to any of the embodiments disclosed herein.

Beneficially, the lipid nanoparticles can deliver the therapeutic agent to the subject at clinically relevant doses, for example, at a dose of at least 0.3 mg/kg. In some embodiments, that dose at which the present LNPs deliver the therapeutic agent is about 0.01 to about 3.0 mg/kg. For example the dose at which the therapeutic agent is delivered may be about 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.35, 0.4, 0.45, 0.5, 0.55, 0.6, 0.65, 0.7, 0.75, 0.8, 0.9, 1.0, 1.1, 1.2, 1.3, 1.4, 1.5 1.6, 1.7, 1.8, 1.9, 2.0, 2.1, 2.2, 2.3, 2.4, 2.5, 2.6, 2.7, 2.9, 2.9, or 3.0 mg/kg.

The present disclosure also provides compositions comprising a lipid nanoparticle according to any of the embodiments described herein, and a pharmaceutically acceptable carrier. As used herein, the term "pharmaceutically acceptable carrier" preferably refers to a material that can be incorporated into a composition and administered to a patient without causing unacceptable biological effects or interacting in an unacceptable manner with other components of the composition. Such pharmaceutically acceptable materials typically have met the required standards of toxicological and manufacturing testing, and include those materials identified as suitable inactive ingredients by the U.S. Food and Drug Administration.

Thus, the LNPs according to the present disclosure may be provided in a composition that is formulated for any type of administration. For example, the compositions may be formulated for administration orally, topically, parenterally, enterally, or by inhalation (e.g., intranasally). The active agent may be formulated for neat administration, or in combination with conventional pharmaceutical carriers, diluents, or excipients, which may be liquid or solid. The applicable solid carrier, diluent, or excipient may function as, among other things, a binder, disintegrant, filler, lubricant, glidant, compression aid, processing aid, color, sweetener, preservative, suspensing/dispersing agent, tablet-disintegrating agent, encapsulating material, film former or coating, flavoring agent, or printing ink. Any material used in preparing any dosage unit form is preferably pharmaceutically pure and substantially non-toxic in the amounts employed. In addition, the LNPs may be incorporated into sustained-release preparations and formulations. Administration in this respect includes administration by, inter alia, the following routes: intravenous, intramuscular, subcutaneous, intraocular, intrasynovial, transepithelial including transdermal, ophthalmic, sublingual and buccal; topically including ophthalmic, dermal, ocular, rectal and nasal inhalation via insufflation, aerosol, and rectal systemic.

In powders, the carrier, diluent, or excipient may be a finely divided solid that is in admixture with the finely divided active ingredient. In tablets, the LNPs are mixed with a carrier, diluent or excipient having the necessary compression properties in suitable proportions and compacted in the shape and size desired. For oral therapeutic administration, the LNPs may be incorporated with the carrier, diluent, or excipient and used in the form of ingestible tablets, buccal tablets, troches, capsules, elixirs, suspensions, syrups, wafers, and the like. The amount of LNP in such therapeutically useful compositions is preferably such that a suitable dosage will be obtained.

Liquid carriers, diluents, or excipients may be used in preparing solutions, suspensions, emulsions, syrups, elixirs, and the like. The LNPs may be suspended in a pharmaceutically acceptable liquid such as water, an organic solvent, a mixture of both, or pharmaceutically acceptable oils or fat. The liquid carrier, excipient, or diluent can contain other suitable pharmaceutical additives such as solubilizers, emulsifiers, buffers, preservatives, sweeteners, flavoring agents, suspending agents, thickening agents, colors, viscosity regulators, stabilizers, or osmo-regulators.

Suitable solid carriers, diluents, and excipients may include, for example, calcium phosphate, silicon dioxide, magnesium stearate, talc, sugars, lactose, dextrin, starch, gelatin, cellulose, methyl cellulose, ethylcellulose, sodium carboxymethyl cellulose, microcrystalline cellulose, polyvinylpyrrolidine, low melting waxes, ion exchange resins, croscarmellose carbon, acacia, pregelatinized starch, crospovidone, HPMC, povidone, titanium dioxide, polycrystalline cellulose, aluminum methahydroxide, agar-agar, tragacanth, or mixtures thereof.

Suitable examples of liquid carriers, diluents, and excipients, for example, for oral, topical, or parenteral administration, include water (particularly containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil), or mixtures thereof.

For parenteral administration, the carrier, diluent, or excipient can also be an oily ester such as ethyl oleate and isopropyl myristate. Also contemplated are sterile liquid carriers, diluents, or excipients, which are used in sterile liquid form compositions for parenteral administration. Solutions of the LNPs can be prepared in water suitably mixed with a surfactant, such as hydroxypropylcellulose. A dispersion can also be prepared in glycerol, liquid polyethylene glycols, and mixtures thereof and in oils. Under ordinary conditions of storage and use, these preparations may contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. In all cases, the form is preferably sterile and fluid to provide easy syringability. It is preferably stable under the conditions of manufacture and storage and is preferably preserved against the contaminating action of microorganisms such as bacteria and fungi. The carrier, diluent, or excipient may be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating, such as lecithin, by the maintenance of the required particle size in the case of a dispersion, and by the use of surfactants. The prevention of the action of microorganisms may be achieved by various antibacterial and antifungal agents, for example, parabens, chlorobutanol, phenol, sorbic acid, thimerosal, and the like. In some instances, the antimicrobial peptides themselves may be sufficient to prevent contamination by microorganisms. In many cases, it will be preferable to include isotonic agents, for example, sugars or sodium chloride. Prolonged absorption of the injectable compositions may be achieved by the use of agents delaying absorption, for example, aluminum monostearate and gelatin.

Sterile injectable solutions may be prepared by incorporating the LNPs in the pharmaceutically appropriate amounts, in the appropriate solvent, with various of the other ingredients enumerated above, as required, followed by filtered sterilization. Generally, dispersions may be prepared by incorporating the LNPs into a sterile vehicle which contains the basic dispersion medium and the required other ingredients from those enumerated above. In the case of sterile powders for the preparation of sterile injectable solutions, the preferred methods of preparation may include vacuum drying and freeze drying techniques that yield a powder of the LNPs or ingredients, plus any additional desired ingredient from the previously sterile-filtered solution thereof.

EXAMPLES

The present invention is further defined in the following Examples. It should be understood that these examples, while indicating preferred embodiments of the invention, are given by way of illustration only, and should not be construed as limiting the appended claims. From the above discussion and these examples, one skilled in the art can ascertain the essential characteristics of this invention, and without departing from the spirit and scope thereof, can make various changes and modifications of the invention to adapt it to various usages and conditions.

Example 1—Design and Characterization of Ionizable Lipids

Ionizable lipids consisting of a piperazine core and two tertiary amines as ionizable headgroups linked to hydrophobic carbon chains, which were presently termed "Pi-Lipids", were designed (FIG. 1A). Ester bonds were originally selected as linkers; however, this synthetic strategy did not afford the expected compounds. Amide bonds were then selected. To the piperazine core, a saturated hydrocarbon chain ranging from C10 to C12 was added. Finally, linoleate-based scaffolds were added to the design. Eight novel piperazine-based ionizable lipids were successfully synthesized (FIG. 1B and FIG. 1C). Briefly, a simple and straightforward amide coupling reaction between 1,4-bis(3-aminopropyl) piperazine and Boc-protected β-Alanine or γ-Aminobutyric acid yielded piperazine intermediates, in 12 hours, with a 50% yield. A subsequent Boc deprotection followed by one-pot reductive amination reaction with different hydrophobic aldehydes led to the final piperazine-based lipids (PPZ) in yields of 32% to 59%. The length of the carbon chain linkage was varied and lipids were synthesized in two scaffolds, PPZ-A containing two carbons as linkage, and PPZ-B containing three carbons. The lipid structures were confirmed by nuclear magnetic resonance (NMR) and high-resolution mass spectrometry (HRMS) (FIG. 1B).

Synthesis of Intermediate.

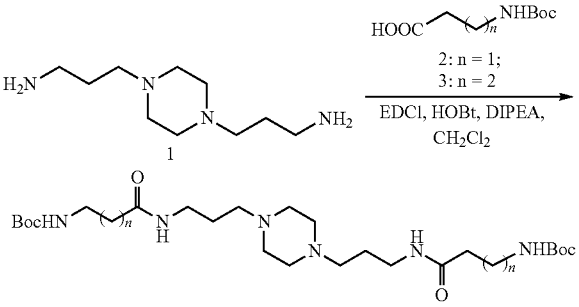

4: n = 1
5: n = 2

To a mixture of 2 or 3 (4.5 mmol) in 10 mL $CH_2Cl_2$ was added DIPEA (4.5 mmol), followed by EDCI (4.5 mmol) and HOBt (4.5 mmol). The mixture was stirred at room temperature for 10 min and then was added 1 (1.5 mmol) dropwise. The resulting mixture was stirred at room temperature for 12 hr and quenched by the addition of saturated NaHCO3 solution (20 mL). The aqueous phase was extracted with $CH_2Cl_2$ (20 mL) three times and concentrated in vacuo. The crude product was then purified by column chromatography using eluent $CH_2Cl_2$/MeOH (10:1).

4: white solid, yield 50%. $^1H$ NMR (500 MHz, $CDCl_3$) δ 7.18 (s, 2H), 5.24 (t, J=6.0 Hz, 2H), 3.39 (q, J=6.2 Hz, 4H), 3.33 (q, J=6.1 Hz, 4H), 2.57-2.42 (m, 8H), 2.35 (t, J=6.0 Hz, 4H), 2.01-1.83 (m, 4H), 1.67 (p, J=6.3 Hz, 4H), 1.42 (s, 18H). $^{13}C$ NMR (125 MHz, $CDCl_3$) δ 171.18, 156.12, 79.24, 57.25, 53.22, 50.82, 39.37, 36.73, 36.36, 28.42, 24.94. HRMS (ESI) m/z calcd for $C_{26}H_{50}N_6O_6$ $[M+H]^+$=543.3864, found=543.3867.

5: white solid, yield 47%. $^1H$ NMR (500 MHz, $CDCl_3$) δ 7.21 (t, J=5.3 Hz, 2H), 4.90 (t, J=6.5 Hz, 2H), 3.30 (q, J=5.7 Hz, 4H), 3.13 (q, J=6.6 Hz, 4H), 2.54-2.40 (m, 8H), 2.17 (t, J=7.2 Hz, 4H), 1.78 (p, J=7.0 Hz, 4H), 1.67 (p, J=6.6 Hz, 4H), 1.41 (s, 18H). $^{13}C$ NMR (125 MHz, $CDCl_3$) δ 172.51, 156.41, 79.23, 57.06, 53.27, 50.65, 39.94, 39.10, 33.95, 28.43, 26.31, 25.31. HRMS (ESI) m/z calcd for $C_{28}H_{54}N_6O_6$ $[M+H]^+$=571.4177, found=571.4179.

Example 2—Formulation of Lipid Nanoparticles Using Piperazine Lipids

It was then investigated whether novel Pi-Lipids formulated into stable, monodisperse LNPs, which were termed Pi-LNPs. LNPs may be formulated using four components: (i) an ionizable or cationic lipid, (ii) a PEG-lipid, (iii) a cholesterol, and (iv) a helper lipid. Thus, to isolate the effect of the Pi-Lipids, the LNPs were formulated with components that form stable LNPs with other (i) cationic or ionizable lipids. Specifically, chosen were (ii) two PEG-lipids with different lengths of carbon chains ($C_{14}PEG_{2K}$ and $C_{18}PEG_{2K}$), (iii) two cholesterol variants (cholesterol, 20α-OH cholesterol), and (iv) 1,2-dioleoyl-sn-glycero-3-phosphoethanolamine (DOPE) (FIG. 1B). Because LNP formation and stability can vary with the ratio of these four components, a control was added to ensure results were robust, testing four different molar ratios (FIG. 1D). Thus, using microfluidics, 128 chemically distinct Pi-LNPs were formulated.

The Pi-LNPs were analyzed using a FIND[26], a DNA barcode-based assay that quantifies how dozens of different LNPs deliver mRNA in up to 30 cell types in vivo. LNP 1, with chemical composition 1, was formulated to carry Cre mRNA and DNA barcode 1, and LNP N, with chemical composition N, to carry Cre mRNA and DNA barcode N. By incorporating a distinct DNA barcode in each individual LNP, it was possible to identify individual LNP delivery through deep sequencing. A quality control step was performed by quantifying the hydrodynamic diameter and polydispersity of all 128 Pi-LNPs individually using dynamic light scattering. Only monodisperse Pi-LNPs with diameters from 20 nm to 200 nm were selected. Of the original 128 Pi-LNPs, 65 met these criteria and were pooled together for subsequent in vivo administration (FIG. 1E).

To understand the effect of chemical structure on Pi-LNP formation, the hydrodynamic diameters were analyzed, observing that lipids with shorter C10 carbon chains formed Pi-LNPs with an average diameter of 96 nm for PPZ-A10 and 100 nm for PPZ-B10. By contrast, lipids with longer carbon chains ($C_{18}$) formed LNPs with larger diameters, including 134 nm for PPZ-A-18-2Z and 155 nm for PPZ-B-18-2Z (FIG. 1F). It was found that while the Pi-LNP diameter did seem to vary with the structure of the Pi-Lipid, the diameter did not change as a function of the cholesterol (FIG. 1G). Finally, the diameter of the pool of Pi-LNPs was tested, and the pool was found to be within the range of the diameters of the 65 Pi-LNPs, suggesting that mixing the Pi-LNPs together did not cause them to come out of solution (FIG. 1H). Taken together, these data permitted the conclusion that novel Pi-Lipids can form monodisperse, stable Pi-LNPs.

Synthesis of PPZ Ionizable Lipids.

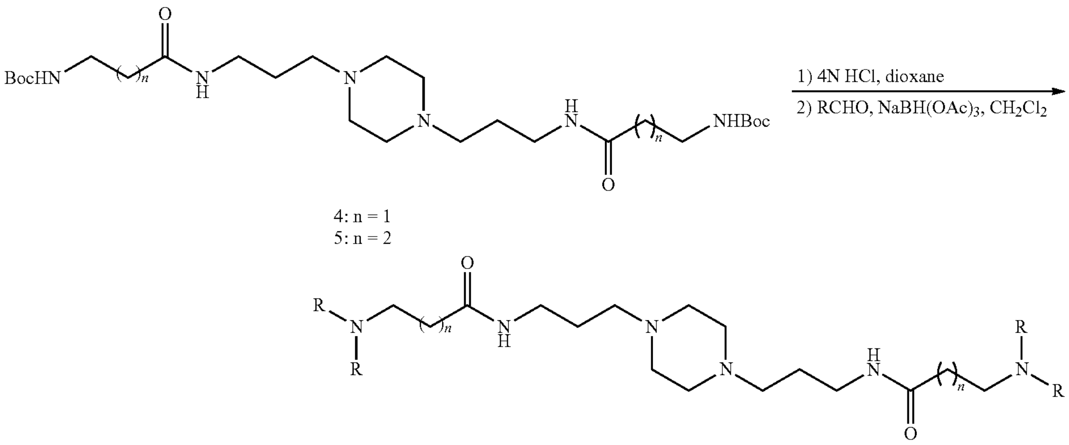

4: n = 1
5: n = 2

PPZ-A or PPZ-B

To the intermediate 4 or 5 (0.1 mmol) was added 3 mL 4N HCl in dioxane at 0° C. and the mixture was stirred at room temperature for 1 hr. Solvent was removed in vacuo and the crude product was dissolved in 1 mL $CH_2Cl_2$. Aldehyde RCHO (0.6 mmol) was added followed by $NaBH(OAc)_3$ (0.5 mmol). The resulting mixture was stirred at room temperature for 12 hr and then purified by column chromatography using $CH_2C_{12}$/MeOH (10:1 to 5:1).

PPZ-A10: colorless oil, yield 56%. $^1$H NMR (500 MHz, $CDCl_3$) δ 8.52 (t, J=5.6 Hz, 2H), 3.23 (q, J=6.6 Hz, 4H), 2.63 (t, J=6.1 Hz, 4H), 2.57-2.24 (m, 24H), 1.70-1.61 (m, 4H), 1.46-1.36 (m, 8H), 1.30-1.18 (m, 54H), 0.86 (t, J=6.9 Hz, 12H). $^{13}$C NMR (125 MHz, $CDCl_3$) δ 172.66, 56.33, 53.25, 53.22, 50.26, 37.52, 32.74, 31.84, 29.62, 29.54, 29.27, 27.58, 26.72, 26.49, 22.62, 14.06. HRMS (ESI) m/z calcd for C56H114N6O2 $[M+2H]^{2+}$=452.4574, found=452.4570.

PPZ-A11: colorless oil, yield 59%. $^1$H NMR (500 MHz, $CDCl_3$) δ 8.52 (t, J=5.6 Hz, 2H), 3.23 (q, J=6.7 Hz, 4H), 2.63 (t, J=6.1 Hz, 4H), 2.56-2.21 (m, 24H), 1.65 (q, J=7.2 Hz, 4H), 1.47-1.36 (m, 10H), 1.31-1.17 (m, 66H). $^{13}$C NMR (125 MHz, $CDCl_3$) δ 172.69, 56.40, 53.31, 53.29, 50.32, 37.59, 32.82, 31.91, 29.68, 29.65, 29.63, 29.60, 29.35, 28.40, 27.64, 26.79, 26.56, 22.69, 14.13. HRMS (ESI) m/z calcd for C60H122N6O2 $[M+2H]^{2+}$=480.4887, found=480.4886.

PPZ-A12: colorless oil, yield 47%. $^1$H NMR (500 MHz, $CDCl_3$) δ 8.50 (t, J=5.6 Hz, 2H), 3.23 (q, J=6.7 Hz, 4H), 2.64 (t, J=6.1 Hz, 4H), 2.59-2.20 (m, 24H), 1.65 (p, J=7.1 Hz, 4H), 1.48-1.33 (m, 9H), 1.32-1.11 (m, 75H), 0.85 (t, J=6.9 Hz, 12H). $^{13}$C NMR (125 MHz, $CDCl_3$) δ 172.66, 56.40, 53.30, 53.28, 50.31, 37.60, 32.80, 31.92, 29.68, 29.65, 29.60, 29.36, 27.63, 26.76, 26.52, 22.69, 14.12. HRMS (ESI) m/z calcd for C64H130N6O2 $[M+2H]^{2+}$=508.5200, found=508.5201.

PPZ-A18-2Z: colorless oil, yield 38%. $^1$H NMR (500 MHz, $CDCl_3$) δ 8.45 (t, J=5.7 Hz, 2H), 5.43-5.19 (m, 16H), 3.23 (q, J=6.7 Hz, 4H), 2.75 (t, J=6.7 Hz, 8H), 2.66 (t, J=6.1

Hz, 4H), 2.50-2.28 (m, 24H), 2.03 (q, J=7.0 Hz, 16H), 1.71-1.61 (m, 4H), 1.46-1.38 (m, 10H), 1.37-1.21 (m, 62H), 0.87 (t, J=6.9 Hz, 12H). $^{13}C$ NMR (125 MHz, $CDCl_3$) δ 172.61, 130.21, 130.04, 128.04, 127.90, 56.40, 53.30, 53.27, 50.25, 37.64, 32.81, 31.53, 29.67, 29.60, 29.58, 29.35, 29.29, 27.64, 27.23, 27.21, 26.75, 26.46, 25.64, 22.58, 14.10. HRMS (ESI) m/z calcd for C88H162N6O2 $[M+2H]^{2+}$=668.6452, found=668.6450.

PPZ-B10: colorless oil, yield 47%. $^{1}H$ NMR (500 MHz, $CDCl_3$) δ 7.22 (t, J=5.4 Hz, 2H), 3.30 (q, J=6.2 Hz, 4H), 2.81-2.25 (m, 24H), 2.19 (t, J=7.1 Hz, 4H), 1.77 (p, J=7.3 Hz, 3H), 1.66 (p, J=6.5 Hz, 4H), 1.49-1.33 (m, 8H), 1.34-1.17 (m, 56H), 0.87 (t, J=6.9 Hz, 13H). $^{13}C$ NMR (125 MHz, $CDCl_3$) δ 172.77, 57.23, 53.90, 53.48, 53.43, 39.06, 34.91, 31.92, 29.69, 29.64, 29.61, 29.35, 27.60, 26.62, 25.68, 22.88, 22.69, 14.13. HRMS (ESI) m/z calcd for C58H118N6O2 $[M+2H]^{2+}$=466.4731, found=466.4730.

PPZ-B11: colorless oil, yield 44%. $^{1}H$ NMR (500 MHz, $CDCl_3$) δ 7.27 (t, J=5.5 Hz, 2H), 3.29 (q, J=6.1 Hz, 4H), 2.63-2.35 (m, 24H), 2.21 (t, J=7.1 Hz, 4H), 1.80 (p, J=7.1 Hz, 4H), 1.66 (p, J=6.5 Hz, 4H), 1.50-1.40 (m, 8H), 1.34-1.16 (m, 64H), 0.86 (t, J=6.9 Hz, 11H). $^{13}C$ NMR (125 MHz, $CDCl_3$) δ 172.59, 57.17, 53.74, 53.39, 53.33, 39.05, 34.67, 31.92, 29.66, 29.63, 29.57, 29.35, 27.52, 26.23, 25.63, 22.69, 22.54, 14.13. HRMS (ESI) m/z calcd for C62H126N6O2 $[M+2H]^{2+}$=494.5044, found=494.5044.

PPZ-B12: colorless oil, yield 42%. $^{1}H$ NMR (500 MHz, $CDCl_3$) δ 7.26 (t, J=5.7 Hz, 2H), 3.28 (q, J=6.2 Hz, 4H), 2.59-2.30 (m, 24H), 2.19 (t, J=7.1 Hz, 4H), 1.78 (p, J=7.1 Hz, 4H), 1.64 (p, J=6.5 Hz, 4H), 1.47-1.35 (m, 8H), 1.30-1.15 (m, 72H), 0.85 (t, J=6.9 Hz, 12H). $^{13}C$ NMR (125 MHz, $CDCl_3$) δ 172.62, 57.17, 53.77, 53.39, 53.35, 39.03, 34.70, 31.91, 29.67, 29.66, 29.64, 29.58, 29.35, 27.53, 26.32, 25.64, 22.68, 22.61, 14.12. HRMS (ESI) m/z calcd for C66H134N6O2 $[M+2H]^{2+}$=522.5357, found=522.5351.

PPZ-B18-2Z: colorless oil, yield 32%. $^{1}H$ NMR (500 MHz, $CDCl_3$) δ 7.50 (t, J=5.5 Hz, 1H), 5.41-5.25 (m, 16H), 3.27 (q, J=6.1 Hz, 4H), 2.82-2.40 (m, 32H), 2.30 (t, J=6.9 Hz, 4H), 2.02 (q, J=6.9 Hz, 14H), 1.93 (p, J=7.0 Hz, 4H), 1.67 (p, J=6.6 Hz, 4H), 1.61-1.53 (m, 8H), 1.39-1.18 (m, 66H), 0.86 (t, J=6.9 Hz, 12H). $^{13}C$ NMR (125 MHz, $CDCl_3$) δ 171.94, 56.88, 53.15, 53.10, 52.78, 38.92, 31.51, 29.62, 29.47, 29.34, 29.32, 29.20, 27.21, 27.19, 25.63, 25.45, 22.57, 14.09. HRMS (ESI) m/z calcd for C90H166N6O2 $[M+2H]^{2+}$=682.6609, found=682.6608.

Figure 2:
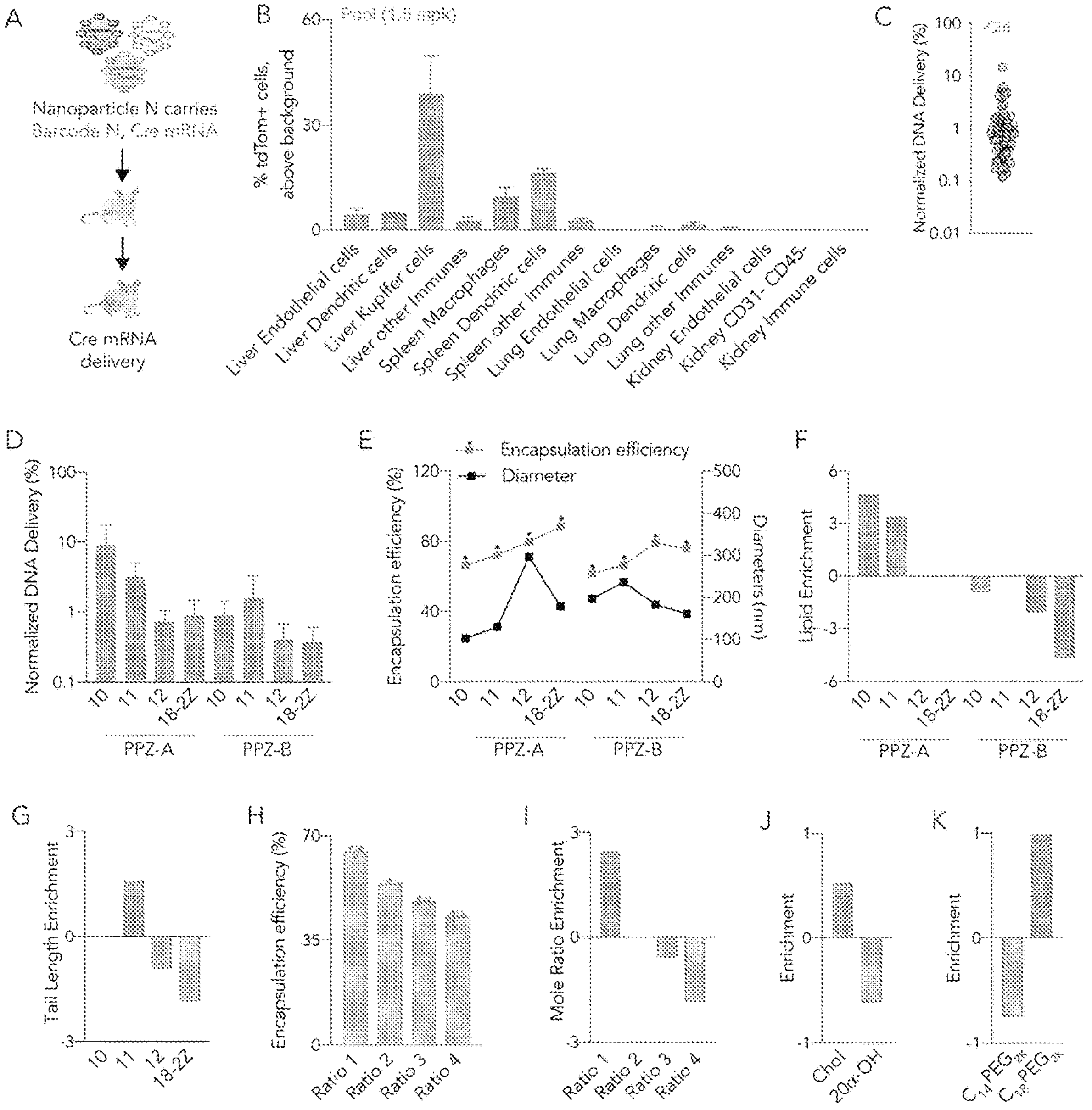
FIGS. 2A-2K provide the results of a study quantifying how 65 LNPs delivered mRNA delivery to 14 cell types in vivo, and subsequent in vivo structure-function analysis.
Figure 4:
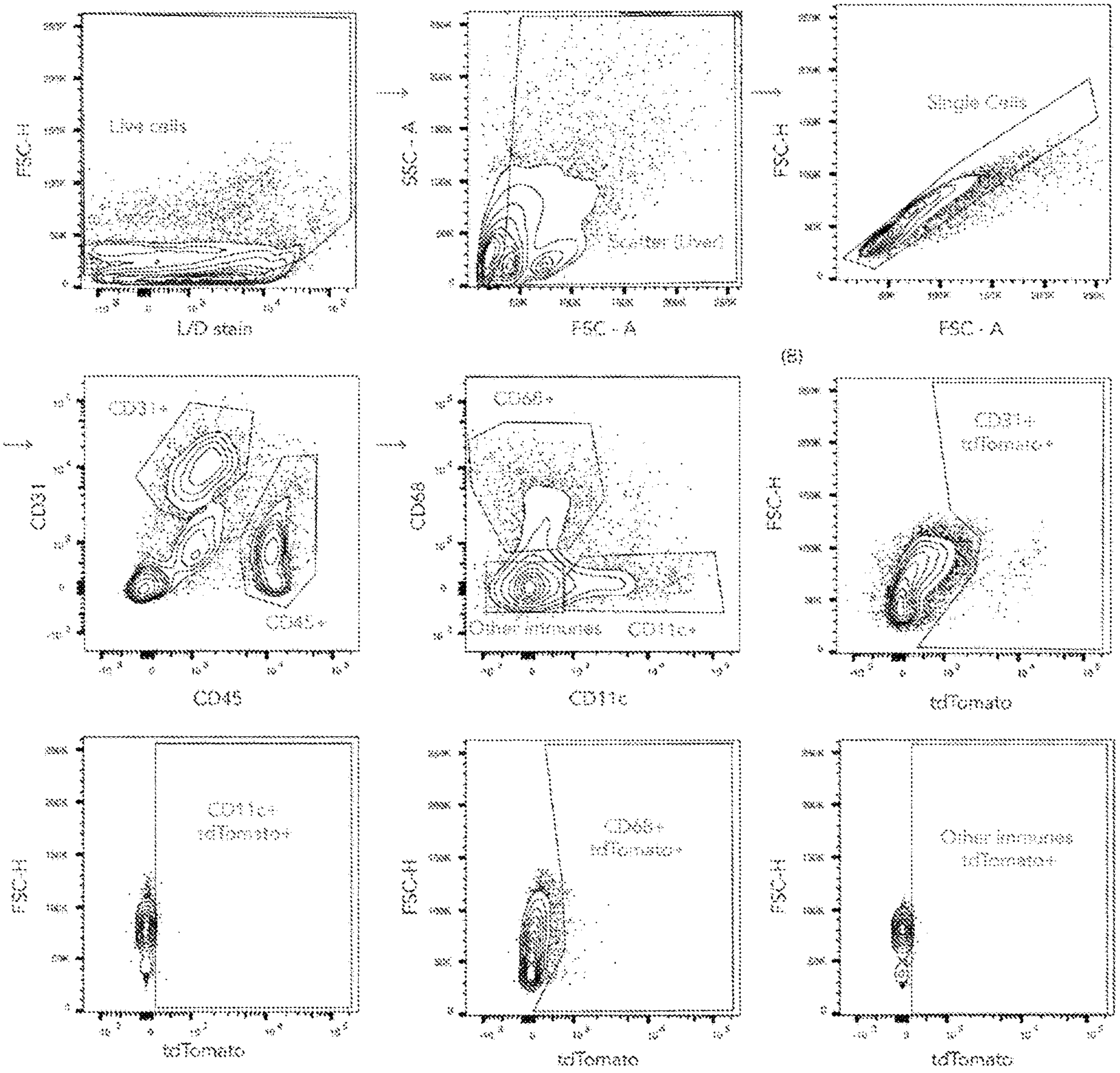
FIG. 4 illustrates representative gating strategies for FACS for cell types in the liver.
Figure 5:
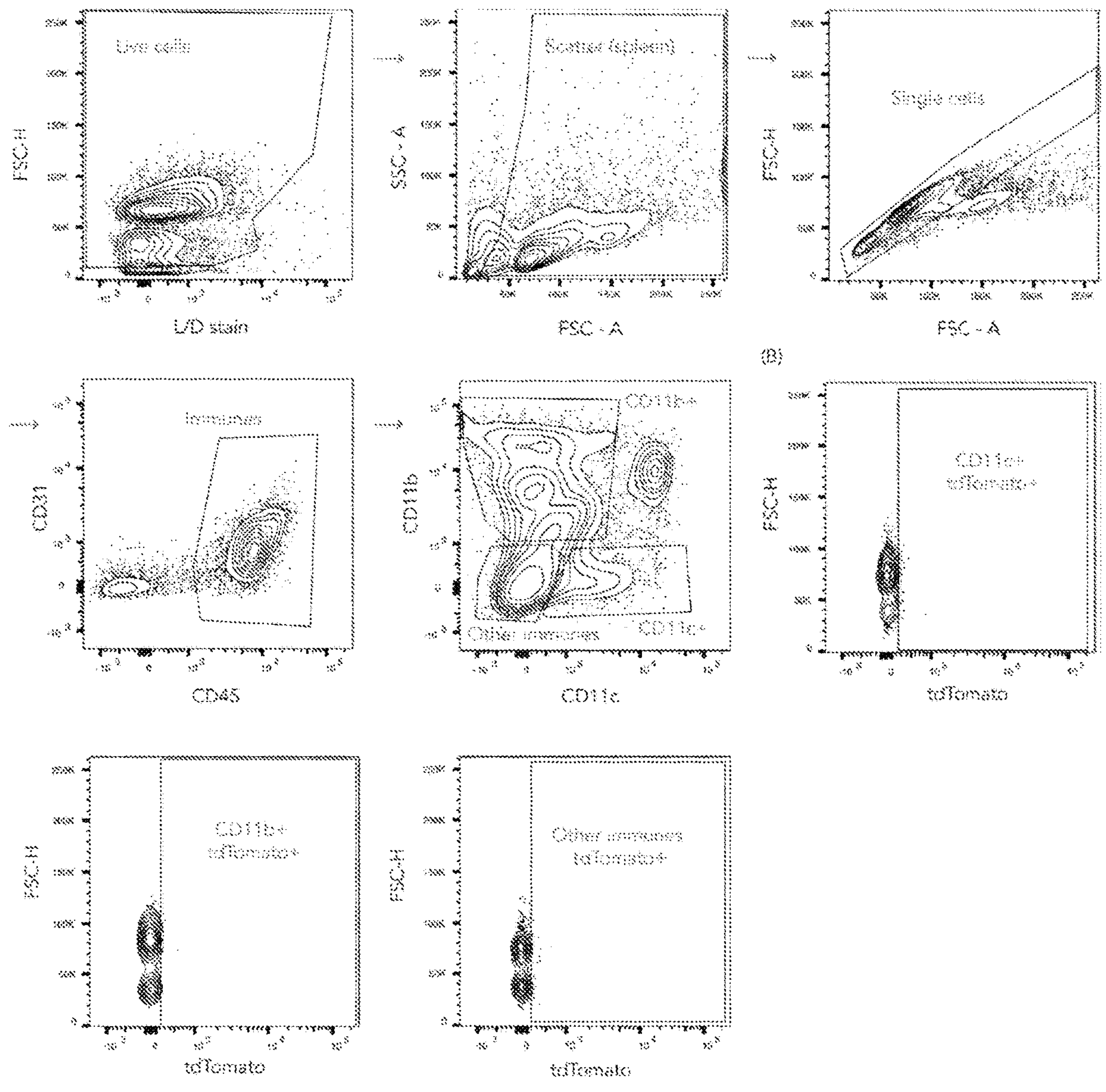
FIG. 5 depicts representative gating strategies for FACS for cell types in the spleen.

Example 3—Delivery of mRNA from Lipid Nanoparticles Formed with Piperazine Lipids Following characterization of the pool of 65 Pi-LNPs, the LNPs were injected into Ai14 mice at a total nucleic dose of 1.5 mg/kg (averaging a 0.023 mg total nucleic acid/kg/particle, for all 65 Pi-LNPs) (FIG. 2A). The Ai14 mice have a Lox-Stop-Lox-tdTomato construct downstream of a CAG promoter. Thus, if Cre mRNA is delivered into a target cell and is subsequently functionally translated into Cre protein, the cells become tdTomato+ (FIG. 2A). By isolating tdTomato+ cells using fluorescence-activated cell sorting (FACS, FIG. 4, FIG. 5) and sequencing the cells using next-generation sequencing, it was possible to isolate the DNA barcodes, associated with specific LNPs, within cells that were functionally transfected with Cre mRNA[26, 36-38]. Three days after injection, liver, spleen, lung, and kidney were isolated and quantified the percentage of tdTomato+ cells from 14 different cell populations (FIG. 2B). It was possible to observe 40% of tdTomato+ cells in Kupffer cells, 10% in spleen macrophages, and 16% in spleen dendritic cells. The percentage of tdTomato+ quantified in liver endothelial cells and dendritic cells was <5%, and no delivery in lung and kidney was observed. After isolating tdTomato+ cells from the most targeted cell populations-Kupffer cells, spleen macrophages, and dendritic cells—it was investigated how well each of the 65 LNPs performed using next-generation DNA sequencing. From the barcode raw counts obtained through sequencing, the normalized delivery of each individual barcode was calculated. Briefly, the normalized delivery of a given barcode was calculated as the number of counts for that barcode divided by the counts for all N barcodes (Tables 1-3, below). Thus, in the first step, the total barcode counts in a given sample are summed. In the second step, the normalized counts for each barcode are calculated as Barcode 1/Sum (Barcode 1->N). In the third step, these normalized counts are normalized a second time by the input DNA. Data from the third step are then plotted as normalized delivery.

TABLE 1

| | | Raw Counts Hepatocytes | | | |
|---|---|---|---|---|---|
| LNP | Barcode | Mouse 1 | Mouse 2 | Mouse 3 | Input |
| 1 | GACACAGT | 100 | 80 | 200 | 100 |
| 2 | GCATAACG | 50 | 45 | 110 | 120 |
| 3 | ACAGAGGT | 120 | 105 | 250 | 110 |
| Total Counts | | 270 | 230 | 560 | 330 |

TABLE 2

| | | Normalized Counts Hepatocytes (%) | | | |
|---|---|---|---|---|---|
| LNP | Barcode | Mouse 1 | Mouse 2 | Mouse 3 | Input |
| 1 | GACACAGT | 37 | 35 | 36 | 30 |
| 2 | GCATAACG | 19 | 20 | 20 | 36 |
| 3 | ACAGAGGT | 44 | 46 | 45 | 33 |
| Total Counts | | 100 | 100 | 100 | 100 |

TABLE 3

| | | Normalized to Input Hepatocytes (%) | | |
|---|---|---|---|---|
| LNP | Barcode | Mouse 1 | Mouse 2 | Mouse 3 |
| 1 | GACACAGT | 40 | 38 | 39 |
| 2 | GCATAACG | 17 | 18 | 18 |
| 3 | ACAGAGGT | 44 | 45 | 44 |
| Total Counts | | 100 | 100 | 100 |

This calculation allowed identification of barcodes that were preferentially delivered to specific cell types, which then indicated LNPs carrying those barcodes. As a control, unencapsulated barcodes were calculated, which were also injected. Since unprotected DNA does not readily enter cells, its normalized delivery was expected to be the lowest among all the barcodes[24], which was the case in this study (FIG. 2C).

Figure 6:
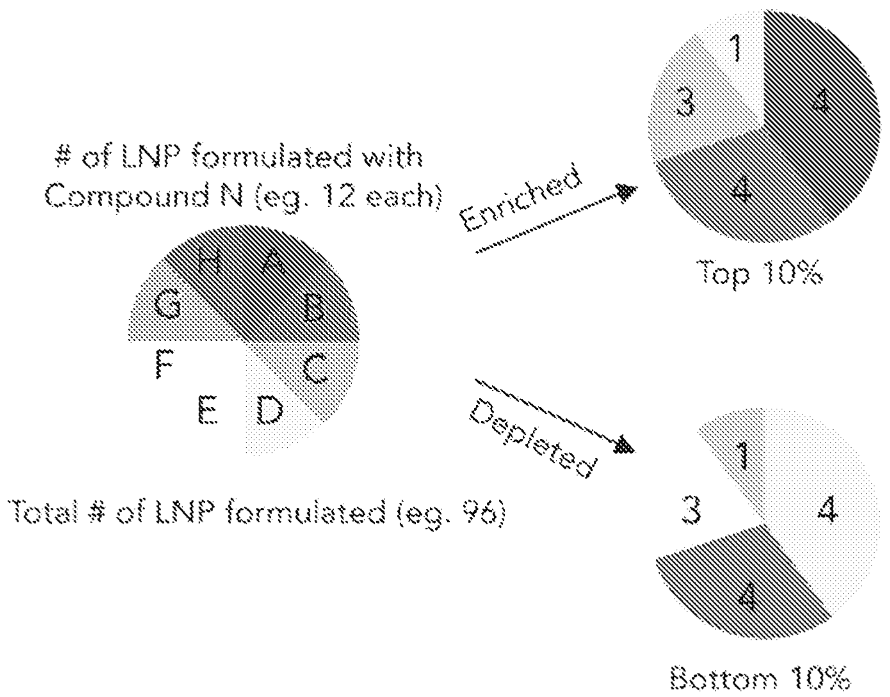
FIG. 6 illustrates an exemplary enrichment calculation.

This large dataset as then used to perform a comprehensive in vivo structure-function analysis. First, the averaged normalized delivery of LNPs was analyzed based on different Pi-Lipid structures and found that Pi-LNPs containing PPZ-A10 exhibited the highest delivery, followed by Pi-LNPs formulated with PPZ-A11 (FIG. 2D). It was hypothesized that the difference in normalized delivery observed between Pi-LNPs could be due to disparities in encapsulation efficiency or LNP diameters. To test this hypothesis, eight LNPs were formulated in which only the ionizable lipid structure was varied while keeping the same molar ratio and compound compositions, and both the diameter and encapsulation efficiency for each LNP were measured (FIG. 2E). Interestingly, an increase of the encapsulation efficiency from 66% to 88% was observed for Pi-LNPs formulated with PPZ-A10 to PPZ-A18-2Z, respectively, demonstrating that the encapsulation efficiency increases with longer carbon chains. However, Pi-LNPs with longer carbon chains also displayed large diameters between 150 and 300 nm, which is unfavorable for LNP delivery[39]. Encapsulation efficiencies between Pi-LNPs formulated with PPZ-A and PPZ-B lipids were comparable, but large diameters were observed for Pi-LNPs containing PPZ-B lipids, most likely explaining the reduced delivery observed for those compounds (FIG. 2D). To complement this structure-function analysis, which included all tested Pi-LNPs, the relationship between Pi-Lipid structure and in vivo activity was analyzed using enrichment (FIG. 2F), which only includes the best and worst nanoparticles. Enrichment, which can be used to understand LNP structure function[40-41], calculates the odds that a material is found in the top or bottom 10% of the LNPs, relative to random chance (FIG. 6). The calculation approach and an exemplary calculation are shown as follows:

$$\frac{\#\text{ of compound } N \text{ in top/bottom } 10\%}{\text{total } \#\text{ of } LNP \times 10\%} \div \frac{\#\text{ of compound } N \text{ formulated in total}}{\text{total } \#\text{ of } LNP} = \text{Enriched}/\textit{depletd}$$

$$\text{Fold of enrichment of compound } N = \text{Compound } N \text{ enriched} - \text{compound } N \text{ depleted}$$

$$\text{e.g. For compound } A \text{ as an example, enriched} - 4/10 \div 12/96 = 3.2;$$

$$\text{depleted} = 0/10 \div 12/96;\ \text{Fold of enrichment} = 3.2$$

Consistent with the normalized delivery data, enrichment analysis highlighted that PPZ-A scaffolds outperformed PPZ-B, and among all lipids, PPZ-A10 was the most enriched. Specifically, it was found that C11 tails were most enriched, compared to other lipid lengths (FIG. 2G). The fold of enrichment for different cholesterol variants and PEG lipids was also analyzed, and it was found that cholesterol outperformed 20α-OH cholesterol (FIG. 2J), and $C_{18}PEG_{2K}$ outperformed $C_{14}PEG_{2K}$ (FIG. 2K). Based on these data, two conclusions were reached: first, that PPZ-A scaffolds outperformed PPZ-B scaffolds; and second, that PPZ-A10, cholesterol, and $C_{18}PEG_{2K}$ could promote delivery to the liver and spleen, relative to the other components that were investigated.

FIGS. 2A-2K therefore illustrate how the 65 LNPs delivered mRNA to 14 cell types in vivo, and provides the subsequent in vivo structure-function analysis. In particular, in FIG. 2A, LNPs were formulated to carry a unique DNA barcode and Cre mRNA. The 65 LNP pool was then administered to Ai14 mice. After 3 days % tdTomato+ cells were quantified in (FIG. 2B) multiple cell types in the liver, spleen, lung, and kidney (N=4/group). FIG. 2C shows normalized delivery for all 65 LNPs, averaged across all samples. Unencapsulated DNA barcode, acting as a negative control (−Ctrl), was delivered into cells less efficiently than barcodes encapsulated by LNPs. FIG. 2D provides normalized delivery of LNPs formulated with each PPZ lipids, average +/−SD. FIG. 2E provides the encapsulation efficiencies and diameters for LNPs formulated with PPZ-A10, cholesterol, $C_{18}PEG_{2K}$, DOPE at a ratio of 35:46.5:2.5:16. FIG. 2F shows the fold enrichment calculated based on different lipids. FIG. 2G provides the fold enrichment calculated based on different tail lengths. FIG. 2H shows the encapsulation efficiencies of LNPs formulated with PPZ-A10, cholesterol, $C_{18}PEG_{2K}$, DOPE at four molar ratios; ratio 1=30:30:1:39; ratio 2=35:46.5:2.5:16; ratio 3=45:39.5:2.5:13; ratio 4=50:35:2.5:12.5, average +/−SEM. FIG. 2I provides the fold enrichment calculated based on different ratios. FIG. 2J shows the fold enrichment calculated for cholesterol and 20α-OH cholesterol. FIG. 2K provides the fold enrichment calculated for $C_{14}PEG_{2K}$ and $C_{18}PEG_{2K}$.

Figure 3:
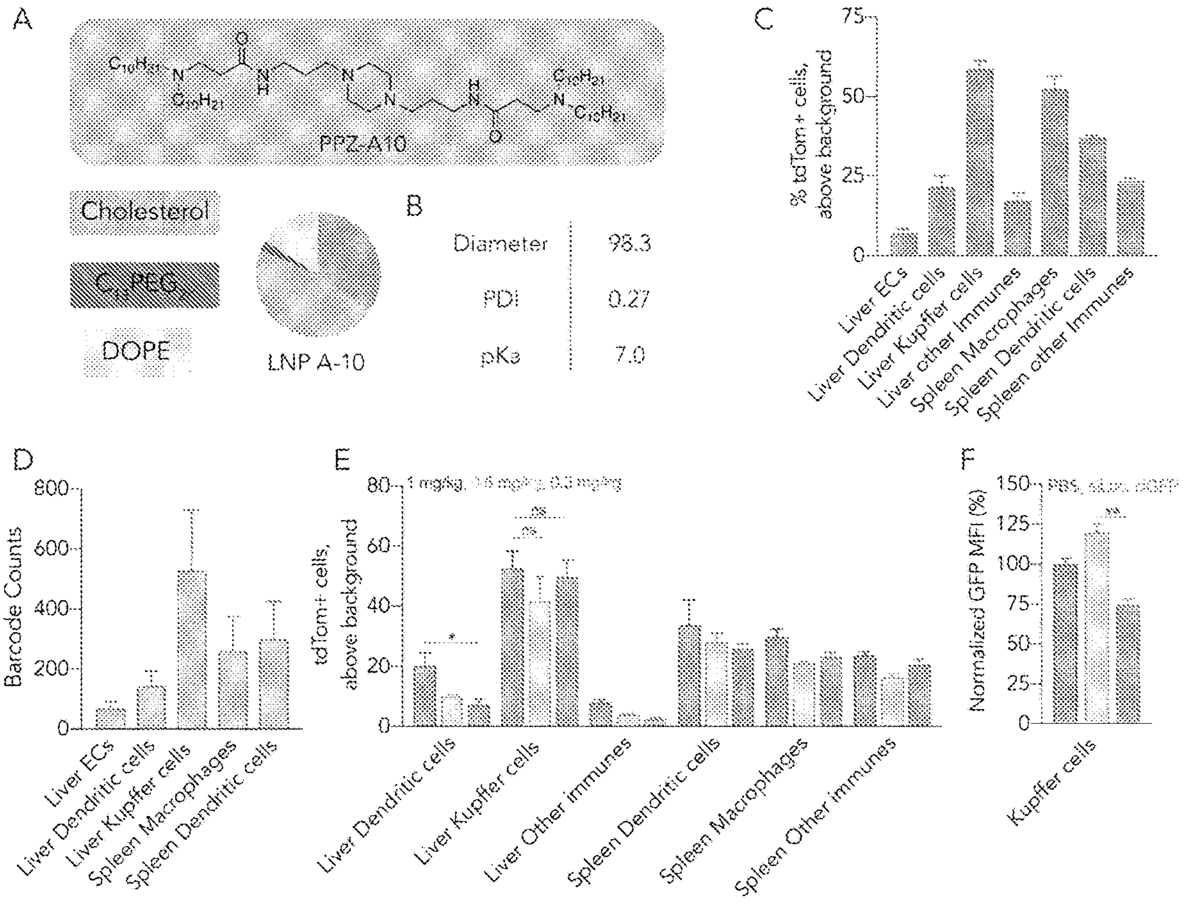
FIGS. 3A-3F provide the results of an investigation demonstrating how LNPs containing piperazine-based lipids deliver mRNA to immune cells.
Figure 7:
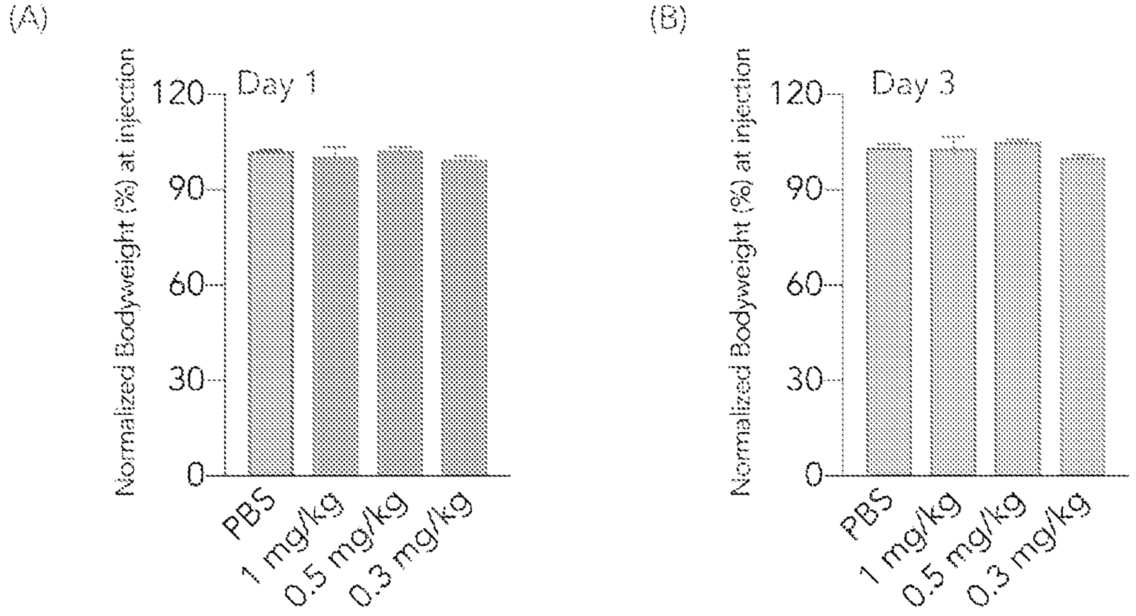
FIG. 7 provides the results of an evaluation of mouse weight at 24 hours and three days following administration of exemplary lipid nanoparticles respectively containing different doses of Cre mRNA.

Based on the in vivo structure-function analysis, a top Pi-LNP was investigated, named LNP-A10 (FIGS. 3A, 3B), which contains the ionizable lipid PPZ-A10, cholesterol, $C_{18}PEG_{2K}$, and DOPE at a ratio of 35:46.5:2.5:16. To validate LNP-A10, it was formulated with Cre mRNA and injected intravenously into Ai14 mice at a dose of 1 mg/kg. Mice weights were monitored throughout the experiment, and no weight loss was observed (FIG. 7). After three days, cells of interest were isolated and the percentage of tdTomato+ cells at the cell-type level were evaluated (FIG. 3C). LNP-A10 successfully delivered Cre mRNA predominantly to 1) Kupffer cells, with 60% tdTomato+ cells observed, 2) spleen macrophages, with 50% tdTomato+ cells, and 3) spleen dendritic cells, with 30% tdTomato+ cells. Also observed was 20% delivery to liver dendritic cells, while the delivery to liver endothelial cells was below 10%. To complement the tdTomato readouts, which quantify the functional delivery of mRNA, the biodistribution of LNP-A10 was measured using QUANT[42], a highly sensitive digital droplet PCR-based method to quantify on- and off-target biodistribution (FIG. 3D). Once again, the distribution of LNP-A10 was found to be the highest in Kupffer cells, followed by spleen dendritic cells and macrophages, which was consistent with the functional delivery results that were observed. It was therefore concluded that LNP-A10 preferentially delivered nucleic acids to hepatic and splenic immune cells.

An in vivo dose response was then performed in order to explore whether LNP-A10 delivered mRNA at 0.3 mg/kg, which is a clinically relevant dose[1]. LNP-A10 including Cre mRNA was injected at doses of 1 mg/kg, 0.5 mg/kg and 0.3 mg/kg (FIG. 3E). At the lowest dose, observed were 50% $tdTomato^+$ Kupffer cells and 23% $tdTomato^+$ splenic macrophages, and 26% $tdTomato^+$ splenic dendritic cells, demonstrating that LNP-A10 can deliver mRNA relevant payloads. Finally, it was evaluated whether LNP-A10 delivered siRNA; notably, it can be difficult to identify a single nanoparticle that efficiently delivers both mRNA and siRNA, due to the distinct biophysical differences between the two payloads[43]. LNPA-10 was therefore formulated with siGFP as well as siLuciferase (siLuc) and injected intravenously into GFP mice at a dose of 1 mg/kg. siLuc, an siRNA that does not interfere with GFP expression, was included as a control to eliminate the possibility of a toxicity-induced decrease in GFP protein expression. About 25% silencing of GFP protein expression was observed in Kupffer cells (FIG. 3F), whereas no silencing was observed in control mice injected with siLuc. This led to the conclusion that LNP-A10 could also deliver siRNA, albeit with lower efficiency than mRNA.

FIGS. 3A-3F therefore illustrate how LNPs containing piperazine-based lipids deliver mRNA to immune cells. In FIG. 3A top-performing LNP-A10 with PPZ-A10, cholesterol, $C_{18}PEG_{2K}$ and DOPE at a ratio of 35:46.5:2.5:16 was identified and formulated with Cre mRNA. In FIG. 3B, the diameter (nm), polydispersity index (PDI), and pKa of LNP-A10. In FIG. 3C, LNP-A10 was injected to Ai14 mice at a dose of 1 mg/kg, and % tdTomato+ cells in liver endothelial cells (ECs), dendritic cells, Kupffer cells, other immunes and spleen macrophages, spleen dendritic cells and spleen other immunes were quantified after three days. N=3/group, average +/−SEM. FIG. 3D provides the biodistribution of LNP-A10 in liver ECs, dendritic cells, Kupffer cells, spleen macrophages and spleen dendritic cells. N=4/group, average +/−SEM. FIG. 3E shows the % tdTomato+ cells in liver dendritic cells, Kupffer cells, liver other immunes and spleen dendritic cells, spleen macrophages and spleen other immunes after treatment of LNP-A10 at doses of 1 mg/kg, 0.5 mg/kg, and 0.3 mg/kg. N=3/group, average +/−SEM. Two-way ANOVA, *$P<0.05$; ns: not significant. FIG. 3F provides the normalized GFP MFI in Kupffer cells after treatment of LNP-A10 carrying siGFP and siLuc at a dose of 1 mg/kg. N=4/group, average +/−SEM. Two-way ANOVA, ** $P<0.01$.

By designing, synthesizing, and characterizing 128 novel Pi-LNPs, it was found that Pi-Lipids can be formulated into stable nanoparticles, and that these nanoparticles can deliver nucleic acids to non-hepatocytes in vivo. Notably, the leading LNP, LNP-A10, that delivered mRNA preferentially to liver and spleen immune cells at a dose as low as 0.3 mg/kg, was identified directly using an in vivo barcoding approach, demonstrating the utility of direct to in vivo high-throughput nanoparticle studies. More broadly, Pi-Lipids and Pi-LNPs generate compelling evidence that bioactive motifs can be added to LNPs without compromising delivery.

References. The following references, to which the preceding disclosure refers using superscripted numerals, may be relevant to the presently disclosed subject matter:

1. Adams, D., et al., Patisiran, an RNAi Therapeutic, for Hereditary Transthyretin Amyloidosis. The New England journal of medicine 2018, 379 (1), 11-21.
2. Balwani, M., et al., Phase 3 Trial of RNAi Therapeutic Givosiran for Acute Intermittent Porphyria. The New England journal of medicine 2020, 382 (24), 2289-2301.
3. Ray, K. K.; Wright, R. S.; Kallend, D.; Koenig, W.; Leiter, L. A.; Raal, F. J.; Bisch, J. A.; Richardson, T.; Jaros, M.; Wijngaard, P. L. J.; Kastelein, J. J. P., Two Phase 3 Trials of Inclisiran in Patients with Elevated LDL Cholesterol. New England Journal of Medicine 2020, 382 (16), 1507-1519.
4 Garrelfs, S. F.; Frishberg, Y.; Hulton, S. A.; Koren, M. J.; O'Riordan, W. D.; Cochat, P.; Deschênes, G.; Shasha-Lavsky, H.; Saland, J. M.; Van't Hoff, W. G.; Fuster, D. G.; Magen, D.; Moochhala, S. H.; Schalk, G.; Simkova, E.; Groothoff, J. W.; Sas, D. J.; Meliambro, K. A.; Lu, J.; Sweetser, M. T.; Garg, P. P.; Vaishnaw, A. K.; Gansner, J. M.; McGregor, T. L.; Lieske, J. C., Lumasiran, an RNAi Therapeutic for Primary Hyperoxaluria Type 1. The New England journal of medicine 2021, 384 (13), 1216-1226.
5. Gillmore, J. D.; Gane, E.; Taubel, J.; Kao, J.; Fontana, M.; Maitland, M. L.; Seitzer, J.; O'Connell, D.; Walsh, K. R.; Wood, K.; Phillips, J.; Xu, Y.; Amaral, A.; Boyd, A. P.; Cehelsky, J. E.; McKee, M. D.; Schiermeier, A.; Harari, O.; Murphy, A.; Kyratsous, C. A.; Zambrowicz, B.; Soltys, R.; Gutstein, D. E.; Leonard, J.; Sepp-Lorenzino, L.; Lebwohl, D., CRISPR-Cas9 In Vivo Gene Editing for Transthyretin Amyloidosis. The New England journal of medicine 2021.
6. Polack, F. P.; Thomas, S. J.; Kitchin, N.; Absalon, J.; Gurtman, A.; Lockhart, S.; Perez, J. L.; Pérez Marc, G.; Moreira, E. D.; Zerbini, C.; Bailey, R.; Swanson, K. A.; Roychoudhury, S.; Koury, K.; Li, P.; Kalina, W. V.; Cooper, D.; Frenck, R. W.; Hammitt, L. L.; Türeci, Ö.; Nell, H.; Schaefer, A.; Ünal, S.; Tresnan, D. B.; Mather, S.; Dormitzer, P. R.; Şahin, U.; Jansen, K. U.; Gruber, W. C., Safety and Efficacy of the BNT162b2 mRNA Covid-19 Vaccine. New England Journal of Medicine 2020, 383 (27), 2603-2615.
7. Baden, L. R.; El Sahly, H. M.; Essink, B.; Kotloff, K.; Frey, S.; Novak, R.; Diemert, D.; Spector, S. A.; Rouphael, N.; Creech, C. B.; McGettigan, J.; Khetan, S.; Segall, N.; Solis, J.; Brosz, A.; Fierro, C.; Schwartz, H.; Neuzil, K.; Corey, L.; Gilbert, P.; Janes, H.; Follmann, D.; Marovich, M.; Mascola, J.; Polakowski, L.; Ledgerwood, J.; Graham, B. S.; Bennett, H.; Pajon, R.; Knightly, C.; Leav, B.; Deng, W.; Zhou, H.; Han, S.; Ivarsson, M.; Miller, J.; Zaks, T., Efficacy and Safety of the mRNA-1273 SARS-COV-2 Vaccine. New England Journal of Medicine 2020.
8. Translate Bio Announces Results from Second Interim Data Analysis from Ongoing Phase 1/2 Clinical Trial of MRT5005 in Patients with Cystic Fibrosis (CF). https://investors.translate.bio/news-releases/news-release-details/translate-bio-announces-results-second-interim-data-analysis. 2021.
9 Translate Bio Announces Pipeline Program Update. https://investors.translate.bio/news-releases/news-release-details/translate-bio-announces-pipeline-program-update. 2019.
10. Braet, F.; Wisse, E., Structural and functional aspects of liver sinusoidal endothelial cell fenestrae: a review. Comp Hepatol 2002, 1 (1), 1-1.
11. Tsoi, K. M.; MacParland, S. A.; Ma, X. Z.; Spetzler, V. N.; Echeverri, J.; Ouyang, B.; Fadel, S. M.; Sykes, E. A.; Goldaracena, N.; Kaths, J. M.; Conneely, J. B.; Alman, B. A.; Selzner, M.; Ostrowski, M. A.; Adeyi, O. A.; Zilman, A.; McGilvray, I. D.; Chan, W. C., Mechanism of hard-nanomaterial clearance by the liver. Nature materials 2016, 15 (11), 1212-1221.
12. Jayaraman, M.; Ansell, S. M.; Mui, B. L.; Tam, Y. K.; Chen, J.; Du, X.; Butler, D.; Eltepu, L.; Matsuda, S.; Narayanannair, J. K.; Rajeev, K. G.; Hafez, I. M.; Akinc, A.; Maier, M. A.; Tracy, M. A.; Cullis, P. R.; Madden, T. D.; Manoharan, M.; Hope, M. J., Maximizing the potency of siRNA lipid nanoparticles for hepatic gene silencing in vivo. Angewandte Chemie 2012, 51 (34), 8529-33.
13. Akinc, A.; Maier, M. A.; Manoharan, M.; Fitzgerald, K.; Jayaraman, M.; Barros, S.; Ansell, S.; Du, X.; Hope, M. J.; Madden, T. D.; Mui, B. L.; Semple, S. C.; Tam, Y. K.; Ciufolini, M.; Witzigmann, D.; Kulkarni, J. A.; van der Meel, R.; Cullis, P. R., The Onpattro story and the clinical translation of nanomedicines containing nucleic acid-based drugs. Nature nanotechnology 2019, 14 (12), 1084-1087.
14. Dammes, N.; Goldsmith, M.; Ramishetti, S.; Dearling, J. L. J.; Veiga, N.; Packard, A. B.; Peer, D., Conformation-sensitive targeting of lipid nanoparticles for RNA therapeutics. Nature nanotechnology 2021.
15. Ramishetti, S.; Hazan-Halevy, I.; Palakuri, R.; Chatterjee, S.; Naidu Gonna, S.; Dammes, N.; Freilich, I.; Kolik Shmuel, L.; Danino, D.; Peer, D., A Combinatorial Library of Lipid Nanoparticles for RNA Delivery to Leukocytes. Advanced materials 2020, 32 (12), e1906128.
16. Kedmi, R.; Veiga, N.; Ramishetti, S.; Goldsmith, M.; Rosenblum, D.; Dammes, N.; Hazan-Halevy, I.; Nahary, L.; Leviatan-Ben-Arye, S.; Harlev, M.; Behlke, M.; Benhar, I.; Lieberman, J.; Peer, D., A modular platform for targeted RNAi therapeutics. Nature nanotechnology 2018, 13 (3), 214-219.
17. Veiga, N.; Goldsmith, M.; Granot, Y.; Rosenblum, D.; Dammes, N.; Kedmi, R.; Ramishetti, S.; Peer, D., Cell specific delivery of modified mRNA expressing therapeutic proteins to leukocytes. Nature communications 2018, 9 (1), 4493.
18. Zuckerman, J. E.; Gritli, I.; Tolcher, A.; Heidel, J. D.; Lim, D.; Morgan, R.; Chmielowski, B.; Ribas, A.; Davis, M. E.; Yen, Y., Correlating animal and human phase Ia/Ib clinical data with CALAA-01, a targeted, polymer-based nanoparticle containing siRNA. Proceedings of the National Academy of Sciences of the U.S. Pat. No. 2,014,111 (31), 11449-54.
19. Akinc, A.; Querbes, W.; De, S.; Qin, J.; Frank-Kamenetsky, M.; Jayaprakash, K. N.; Jayaraman, M.; Rajeev, K. G.; Cantley, W. L.; Dorkin, J. R.; Butler, J. S.; Qin, L.; Racie, T.; Sprague, A.; Fava, E.; Zeigerer, A.; Hope, M. J.; Zerial, M.; Sah, D. W.; Fitzgerald, K.; Tracy, M. A.; Manoharan, M.; Koteliansky, V.; Fougerolles, A.; Maier, M. A., Targeted delivery of RNAi therapeutics with endogenous and exogenous ligand-based mechanisms. Molecular therapy:the journal of the American Society of Gene Therapy 2010, 18 (7), 1357-64.
20. Akinc, A., et al., A combinatorial library of lipid-like materials for delivery of RNAi therapeutics. Nat Biotechnol 2008, 26 (5), 561-9.
21. Dahlman, J. E., et al., In vivo endothelial siRNA delivery using polymeric nanoparticles with low molecular weight. Nat Nano 2014, 9 (8), 648-655.
22. Siegwart, D. J., et al., Combinatorial synthesis of chemically diverse core-shell nanoparticles for intracellular delivery. Proceedings of the National Academy of Sciences of the U.S. Pat. No. 2,011,108 (32), 12996-3001.
23. Paunovska, K.; Sago, C. D.; Monaco, C. M.; Hudson, W. H.; Castro, M. G.; Rudoltz, T. G.; Kalathoor, S.; Vanover, D. A.; Santangelo, P. J.; Ahmed, R.; Bryksin, A. V.; Dahlman, J. E., A Direct Comparison of in Vitro and in Vivo Nucleic Acid Delivery Mediated by Hundreds of Nanoparticles Reveals a Weak Correlation. Nano letters 2018, 18 (3), 2148-2157.
24. Lokugamage, M. P.; Sago, C. D.; Dahlman, J. E., Testing thousands of nanoparticles in vivo using DNA barcodes. Current Opinion in Biomedical Engineering 2018, 7, 1-8.
25. Freitag, F.; Wagner, E., Optimizing synthetic nucleic acid and protein nanocarriers: The chemical evolution approach. Advanced drug delivery reviews 2021, 168, 30-54.
26. Sago, C. D., et al., High-throughput in vivo screen of functional mRNA delivery identifies nanoparticles for endothelial cell gene editing. Proceedings of the National Academy of Sciences 2018.
27. Shaquiquzzaman, M.; Verma, G.; Marella, A.; Akhter, M.; Akhtar, W.; Khan, M. F.; Tasneem, S.; Alam, M. M., Piperazine scaffold: A remarkable tool in generation of diverse pharmacological agents. European journal of medicinal chemistry 2015, 102, 487-529.

28. Magriotis, P. A., Recent progress toward the asymmetric synthesis of carbon-substituted piperazine pharmacophores and oxidative related heterocycles. RSC Med Chem 2020, 11 (7), 745-759.
29. Chilmonczyk, Z.; Krajewski, K. J.; Cybulski, J., Rigid analogues of buspirone and gepirone, 5-HT1A receptors partial agonists. Farmaco 2002, 57 (11), 917-23.
30. Fulton, A.; Norman, T.; Burrows, G. D., Ligand binding and platelet uptake studies of loxapine, amoxapine and their 8-hydroxylated derivatives. J Affect Disord 1982, 4 (2), 113-9.
31. Sharma, P. C.; Jain, A.; Jain, S.; Pahwa, R.; Yar, M. S., Ciprofloxacin: review on developments in synthetic, analytical, and medicinal aspects. Journal of Enzyme Inhibition and Medicinal Chemistry 2010, 25 (4), 577-589.
32. Girase, P. S.; Dhawan, S.; Kumar, V.; Shinde, S. R.; Palkar, M. B.; Karpoormath, R., An appraisal of anti-mycobacterial activity with structure-activity relationship of piperazine and its analogues: A review. European journal of medicinal chemistry 2021, 210, 112967.
33. Love, K. T., et al., Lipid-like materials for low-dose, in vivo gene silencing. Proceedings of the National Academy of Sciences of the U.S. Pat. No. 2,010,107 (5), 1864-9.
34. Semple, S. C., et al., Rational design of cationic lipids for siRNA delivery. Nat Biotechnol 2010, 28 (2), 172-6.
35. Fenton, O. S.; Kauffman, K. J.; McClellan, R. L.; Appel, E. A.; Dorkin, J. R.; Tibbitt, M. W.; Heartlein, M. W.; DeRosa, F.; Langer, R.; Anderson, D. G., Bioinspired Alkenyl Amino Alcohol Ionizable Lipid Materials for Highly Potent In Vivo mRNA Delivery. Advanced materials 2016, 28 (15), 2939-43.
36. Paunovska, K.; Da Silva Sanchez, A. J.; Sago, C. D.; Gan, Z.; Lokugamage, M. P.; Islam, F. Z.; Kalathoor, S.; Krupczak, B. R.; Dahlman, J. E., Nanoparticles Containing Oxidized Cholesterol Deliver mRNA to the Liver Microenvironment at Clinically Relevant Doses. Advanced materials 2019, e1807748.
37. Lokugamage, M. P.; Gan, Z.; Zurla, C.; Levin, J.; Islam, F. Z.; Kalathoor, S.; Sato, M.; Sago, C. D.; Santangelo, P. J.; Dahlman, J. E., Mild Innate Immune Activation Overrides Efficient Nanoparticle-Mediated RNA Delivery. Advanced materials 2019, e1904905.
38. Gan, Z.; Lokugamage, M. P.; Hatit, M. Z. C.; Loughrey, D.; Paunovska, K.; Sato, M.; Cristian, A.; Dahlman, J. E., Nanoparticles containing constrained phospholipids deliver mRNA to liver immune cells in vivo without targeting ligands. Bioeng Transl Med 2020, 5 (3), e10161.
39. Akinc, A.; Goldberg, M.; Qin, J.; Dorkin, J. R.; Gamba-Vitalo, C.; Maier, M.; Jayaprakash, K. N.; Jayaraman, M.; Rajeev, K. G.; Manoharan, M.; Koteliansky, V.; Röhl, I.; Leshchiner, E. S.; Langer, R.; Anderson, D. G., Development of lipidoid-siRNA formulations for systemic delivery to the liver. Molecular therapy:the journal of the American Society of Gene Therapy 2009, 17 (5), 872-9.
40. Sago, C. D.; Lokugamage, M. P.; Islam, F. Z.; Krupczak, B. R.; Sato, M.; Dahlman, J. E., Nanoparticles that deliver RNA to bone marrow identified by in vivo directed evolution. Journal of the American Chemical Society 2018.
41. Paunovska, K., et al., Analyzing 2000 in Vivo Drug Delivery Data Points Reveals Cholesterol Structure Impacts Nanoparticle Delivery. ACS nano 2018, 12 (8), 8341-8349.
42. Sago, C. D.; Lokugamage, M. P.; Lando, G. N.; Djeddar, N.; Shah, N. N.; Syed, C.; Bryksin, A. V.; Dahlman, J. E., Modifying a Commonly Expressed Endocytic Receptor Retargets Nanoparticles in Vivo. Nano letters 2018.
43. Kauffman, K. J., et al., Optimization of Lipid Nanoparticle Formulations for mRNA Delivery in Vivo with Fractional Factorial and Definitive Screening Designs. Nano letters 2015, 15 (11), 7300-6.

What is claimed:

1. A compound of Formula (I):

(I)

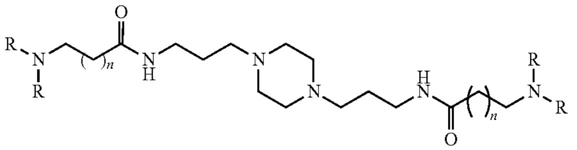

wherein each R is $C_{10-18}$ alkyl or alkenyl;
and,
n is 1 or 2.

2. The compound according to claim 1, wherein each R is the same.

3. The compound according to claim 1, wherein each R is $C_{10}$ alkyl.

4. The compound according to claim 1, wherein each R is $C_{11}$ alkyl.

5. The compound according to claim 1, wherein each R is $C_{18}$ alkenyl.

6. The compound according to claim 5, wherein each R is octadeca-9,12-dienyl.

7. The compound according to claim 1, wherein n=1.

8. The compound according to claim 1, wherein n=2.

9. A lipid nanoparticle comprising a compound of Formula (I) according to claim 1.

10. The lipid nanoparticle according to claim 9, further comprising:
a helper lipid;
a cholesterol;
a polyethylene glycol (PEG) lipid,
or, any combination thereof.

11. The lipid nanoparticle according to claim 9, wherein the lipid nanoparticle delivers the therapeutic agent preferentially to liver or splenic cells of the subject.

12. The lipid nanoparticle according to claim 10, wherein the PEG lipid is $C_{14}PEG_{2K}$ or $C_{18}PEG_{2K}$, or a combination thereof.

13. The lipid nanoparticle according to claim 10, wherein the cholesterol is cholesterol, 20α-OH cholesterol, or a combination thereof.

14. The lipid nanoparticle according to claim 10, wherein the helper lipid is 1,2-dioeoyl-sn-glycero-3-phosphoethanolamine (DOPE).

15. The lipid nanoparticle according to claim 10, wherein the molar ratio of the compound according to Formula (I):the helper lipid:the cholesterol:the PEG lipid is about 30-50:30-47:1-3:12-40.

16. The lipid nanoparticle according to claim 10, wherein the molar ratio of the compound according to Formula (I):the helper lipid:the cholesterol:the PEG lipid is about 30-40:40-47:1-3:12-20.

17. The lipid nanoparticle according to claim 10, wherein the molar ratio of the compound according to Formula (I):the helper lipid:the cholesterol:the PEG lipid is about 35:46.5:2.5:16.

18. The lipid nanoparticle according to claim 9 having a diameter of about 20-200 nm.

19. The lipid nanoparticle according to claim 9, further comprising a therapeutic agent that is encapsulated within the lipid nanoparticle.

20. The lipid nanoparticle according to claim 19, wherein the therapeutic agent is a nucleic acid, oligonucleotide, polynucleotide, protein, peptide, carbohydrate, glycoprotein, lipid, small molecule, or any combination thereof.

21. The lipid nanoparticle according to claim 20, wherein the therapeutic agent is an mRNA.

22. A method comprising administering to a subject a lipid nanoparticle according to claim 9.

23. The method according to claim 22, wherein the lipid nanoparticle delivers the therapeutic agent preferentially to liver or splenic cells of the subject.

24. The method according to claim 23, wherein the lipid nanoparticle delivers the therapeutic agent preferentially to one or more of liver Kupffer cells, spleen dendritic cells, spleen macrophages, liver endothelial cells, or liver dendritic cells of the subject.

25. The method according to claim 22, wherein the lipid nanoparticle delivers the therapeutic agent to the subject at a dose of at least 0.3 mg/kg.

26. A method for delivering a therapeutic agent to liver or splenic cells of a subject comprising administering to the subject a lipid nanoparticle according to claim 19.

27. A composition comprising a lipid nanoparticle according to claim 9 and a pharmaceutically acceptable carrier.

* * * * *